(12) United States Patent
Friedman et al.

(10) Patent No.: US 6,613,005 B1
(45) Date of Patent: Sep. 2, 2003

(54) SYSTEMS AND METHODS FOR STEERING A FOCUSED ULTRASOUND ARRAY

(75) Inventors: Zvi Friedman, Qiriat Bialik (IL); Dov Maor, Haifa (IL)

(73) Assignee: InSightec-TxSonics, Ltd., Tirat Carmel (IL)

( * ) Notice: Subject to any disclaimer, the term of this patent is extended or adjusted under 35 U.S.C. 154(b) by 321 days.

(21) Appl. No.: 09/724,716

(22) Filed: Nov. 28, 2000

(51) Int. Cl.[7] .................................................. A61H 1/00
(52) U.S. Cl. ........................... 601/2; 600/407; 600/371; 600/443; 600/459; 600/462
(58) Field of Search .................. 601/2; 600/407, 600/411, 427, 371, 437, 431, 443, 459, 462, 463, 467

(56) References Cited

U.S. PATENT DOCUMENTS

| | | |
|---|---|---|
| 4,646,756 A | 3/1987 | Watmough et al. |
| 4,647,808 A | 3/1987 | Shibuya ....................... 310/329 |
| 4,858,613 A * | 8/1989 | Fry et al. ............... 128/660.03 |
| 4,957,099 A * | 9/1990 | Hassler ....................... 128/24 A |
| 5,266,863 A | 11/1993 | Nonami et al. ............. 310/339 |
| 5,752,515 A * | 5/1998 | Jolesz et al. ............. 128/653.1 |
| 5,817,021 A | 10/1998 | Reichenberger |

FOREIGN PATENT DOCUMENTS

WO WO 00/78232 A1 12/2000

\* cited by examiner

*Primary Examiner*—Teresa Walberg
*Assistant Examiner*—Shawntina Fuqua
(74) *Attorney, Agent, or Firm*—Bingham McCutchen LLP

(57) ABSTRACT

A focused ultrasound system includes a transducer array including a plurality of sub-arrays, each sub-array defining an acoustic emission surface and including a plurality of transducer elements thereon. A mechanical controller is coupled to the sub-arrays that includes actuators for moving the sub-arrays to adjust an orientation of the acoustic emission surfaces of respective sub-arrays to facilitate steering of acoustic energy emitted by the transducer elements towards a target tissue region. Drive circuitry provides drive signals to the transducer elements, whereby the transducer elements emit acoustic energy from their respective acoustic emission surfaces to ablate the target region, such as a tumor within a patient's brain.

23 Claims, 2 Drawing Sheets

SYSTEMS AND METHODS FOR STEERING A FOCUSED ULTRASOUND ARRAY

FIELD OF THE INVENTION

The present invention relates generally to systems and methods for performing noninvasive procedures using focused ultrasound, and more particularly to systems and methods for controlling or steering a multiple element focused ultrasound transducer array.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors, thereby obviating the need for invasive surgery. For this purpose, piezoelectric transducers have been suggested that may be placed external to the patient but in generally close proximity to the tissue to be ablated and driven by electric signals to produce ultrasonic energy. The transducer is geometrically shaped and positioned such that the ultrasonic energy is focused at a "focal zone") corresponding to a target tissue region within the patient, heating the target tissue region until the tissue is necrosed. The transducer may be sequentially focused and activated at a number of focal zones in close proximity to one another. This series of sonications may be used to cause coagulation necrosis of an entire tissue structure, such as a tumor, of a desired size and shape.

A spherical cap transducer array has been suggested for this purpose that includes a plurality of concentric rings disposed on a curved surface having a radius of curvature defining a portion of a sphere. The concentric rings may be divided circumferentially into a plurality of curved transducer elements or sectors, creating a tiling of the transducer face. The transducer elements are driven by radio frequency (RF) electrical signals at a single frequency offset in phase and amplitude. In particular, the phase and amplitude of the respective drive signals may be controlled so as to focus the emitted ultrasonic energy at a desired "focal distance," i.e., the distance from the transducer to the center of the focal zone and provide a desired energy level in the target tissue region.

In addition, the phase of the respective drive signals to each of the sectors may be controlled to create a desired size and shape for the focal zone. For example, if each of the sectors are driven with respective drive signals that are in phase with one another ("mode 0"), the ultrasonic energy may be focused substantially at a relatively narrow focal zone. Alternatively, the sectors may be driven with respective drive signals that are in a predetermined phase relationship with one another (referred to as "mode n"). This results in a focal zone generally defining an annular shape, creating a wider focus that causes necrosis of a larger tissue region within a focal plane intersecting the focal zone.

Directing acoustic energy through irregular tissue structures, such as bone, may further complicate focusing the acoustic energy at a desired tissue region to be treated. For example, when treating tissue within a skull, the non-uniform interior surface of the skull may cause irregular phase shifts in acoustic energy as it passes through different regions of the skull. It may be difficult to compensate for these irregularities, requiring special calibration of the transducer.

Even if the transducer is calibrated to compensate for aberrations caused by such irregularities, the focus may need to be moved during treatment to focus the acoustic energy at one or more target tissue regions. One option for moving the focal zone is to physically move the transducer with respect to the anatomical structure. Such "mechanical" steering may be used, for example, to control a hemispherical transducer for treating the skull. However, this requires that the transducer be substantially larger than the skull, e.g., about thirty centimeters (30 cm) or more in diameter, in order to provide sufficient freedom of movement. In addition, the space between the transducer and the skull must be substantially filled with a fluid to acoustically couple the transducer and the skull, which may complicate such a steering system.

Alternatively, electronic steering may be used, similar to that described above, in which the relative phase of the acoustic energy emitted by transducer elements making up the transducer is controlled to move the focal zone. The degree of control provided by such electronic steering is inversely proportional to the size of the individual transducer elements. For example, it is generally desirable to have the size of the transducer elements be on the order of the wavelength of the acoustic energy emitted by the array, and preferably as small as half the wavelength, in order to effectively steer the focal zone. Thus, with acoustic energy having a wavelength on the order of two millimeters (2 mm), as is often used for focused ultrasound systems, transducer elements having a similar size, i.e., about two millimeters or less in cross-section would be needed for effective steering.

For an exemplary transducer array having a radius of six centimeters (6 cm) and a desired focal distance of about twelve centimeters (12 cm), this would require approximately three thousand (3,000) elements. Even more dramatically, for an array formed as half of a sphere sized to fit around a skull, this may require as many as about twelve thousand (12,000) elements, which would be prohibitively expensive to make and complicated to operate.

Accordingly, it is desirable to provide systems and methods for treating a tissue region using a multiple element focused ultrasound array that facilitate improved control and/or focusing of the elements in the transducer array.

SUMMARY OF THE INVENTION

The present invention is directed to systems and methods for performing a diagnostic or therapeutic procedure using focused ultrasound, and more particularly to systems and methods for mechanically steering or otherwise controlling a multiple element transducer array to facilitate focusing of the transducer array at one or more regions during a therapeutic ultrasound procedure.

In accordance with one aspect of the present invention, a system is provided that includes a transducer array including a plurality of sub-arrays, each sub-array defining an acoustic emission surface and including one or more, and preferably a plurality of, transducer elements configured for emitting acoustic energy from the acoustic emission surface, each sub-array being independently rotatable with respect to one another. In a preferred embodiment, each sub-array includes a gimbal apparatus pivotably fixing the sub-arrays with respect to one another, for example, to a common support structure.

Drive circuitry is coupled to the transducer elements, the drive circuitry configured for providing respective drive signals to the transducer elements, whereby the transducer elements may emit acoustic energy from their respective acoustic emission surfaces. An electronic controller may be coupled to the drive circuitry, the electronic controller configured for controlling phase shift values and amplitudes of the respective drive signals to further focus the acoustic energy emitted by the transducer elements towards the target region. For example, the electronic controller may be configured for controlling phase shift values of the drive signals to the transducer elements of a respective sub-array for controlling a focal distance of the acoustic energy emitted by the transducer elements in the respective sub-array. Preferably, the electronic controller controls phase shift values of the drive signals between respective transducer elements of each sub-array and/or between respective sub-arrays, e.g., to control a focal distance of the focal zone generated by the transducer array.

A mechanical controller is coupled to the sub-arrays that is configured for moving the sub-arrays to adjust an orientation of the acoustic emission surfaces of respective sub-arrays to facilitate focusing of the acoustic energy emitted by the transducer elements towards the target region. In a preferred embodiment, the mechanical controller includes an actuator coupled to each of the sub-arrays for mechanically steering the respective sub-array to adjust its orientation. More preferably, the mechanical controller may include a pair of actuators coupled to each sub-array, the pair of actuators configured for pivoting the respective sub-array in substantially orthogonal directions.

The transducer array may be mounted within a fluid-filled casing, for example, having a substantially concave shape. In a preferred embodiment, the casing has a substantially concave inner contact surface configured for substantially engaging a skull of a patient. The sub-arrays are preferably arranged within the casing such that the acoustic emission surfaces of the sub-arrays are generally oriented towards the inner contact surface.

The system may be used to perform a therapeutic procedure, such as an ablation procedure, in a target tissue region. Alternatively, the system may be used to perform a therapeutic procedure, e.g., involving acoustic energy of lower intensity than that generally used to ablate tissue, or a diagnostic procedure, e.g., ultrasound imaging.

The transducer elements may be driven with respective drive signals such that the transducer elements emit acoustic energy towards a target region. Prior to or while activating the transducer elements, the sub-arrays may be steered with respect to one another to focus the acoustic energy generated by the transducer elements towards the target region. For example, the sub-arrays may be pivoted about respective fixed points to adjust an angular orientation of their respective acoustic emission surfaces. Preferably, the sub-arrays are pivoted about two respective axes of rotation that are substantially perpendicular to one another.

In a preferred method, the transducer array is acoustically coupled to a skull, for example, by disposing the transducer array around the skull, such that the target region is a tissue structure, such as a tumor, within the skull. The transducer elements are driven with respective drive signals such that the acoustic energy emitted by the transducer element substantially ablates the tissue structure. Phase shift values of drive signals driving the transducer elements of each sub-array may be controlled such that the acoustic energy emitted by the respective sub-array is focused at a predetermined focal distance or is focused at a focal zone having a predetermined shape.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1A:
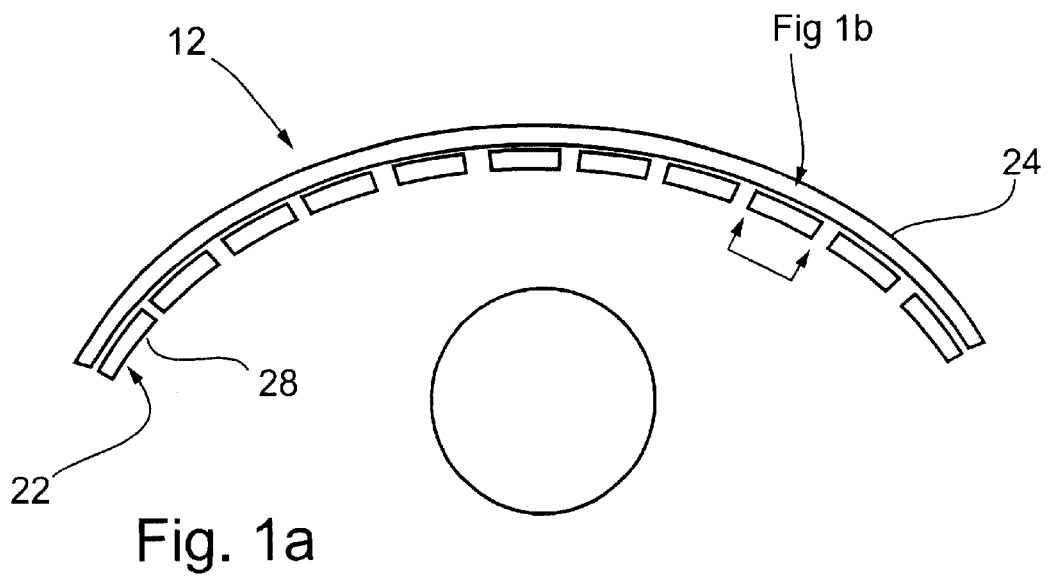
FIG. 1A is a cross-sectional view of a focused ultrasound transducer array disposed about a patient's head, in accordance with the present invention.
Figure 1B:
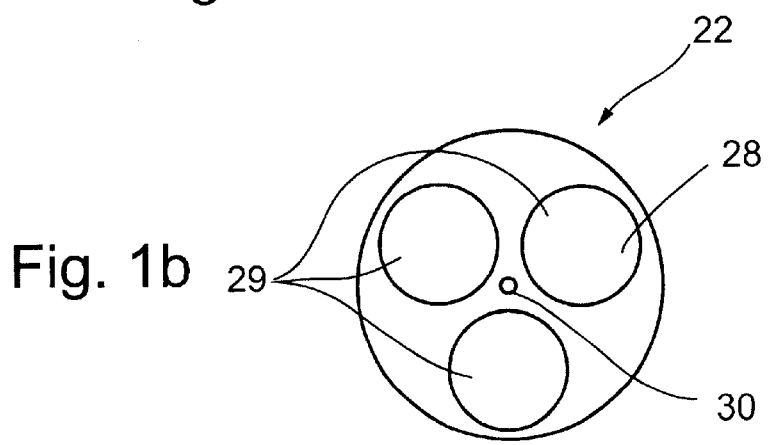
FIG. 1B is a detail, showing a top view of a single sub-array that may be incorporated into the transducer array of FIG. 1A.
Figure 1C:
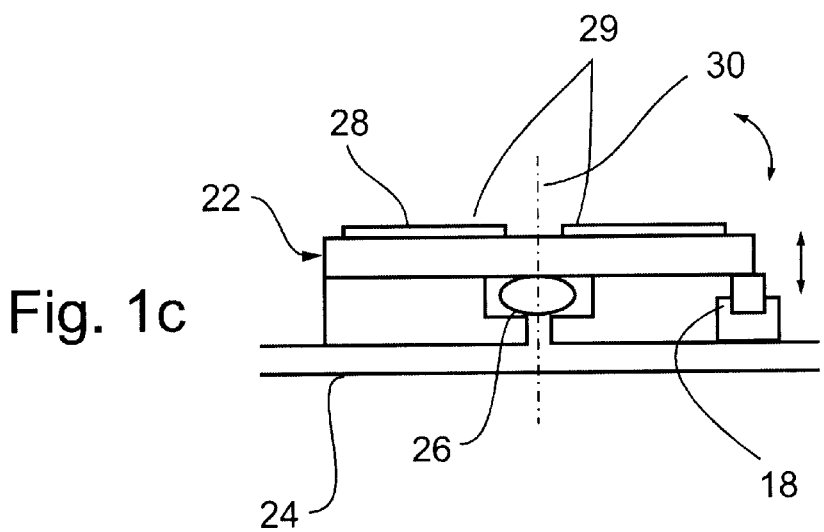
FIG. 1C is a detail, showing a side view of a single sub-array pivotably fixed to a support structure by a gimbal apparatus that may be incorporated into the transducer array of FIG. 1A.
Figure 2:
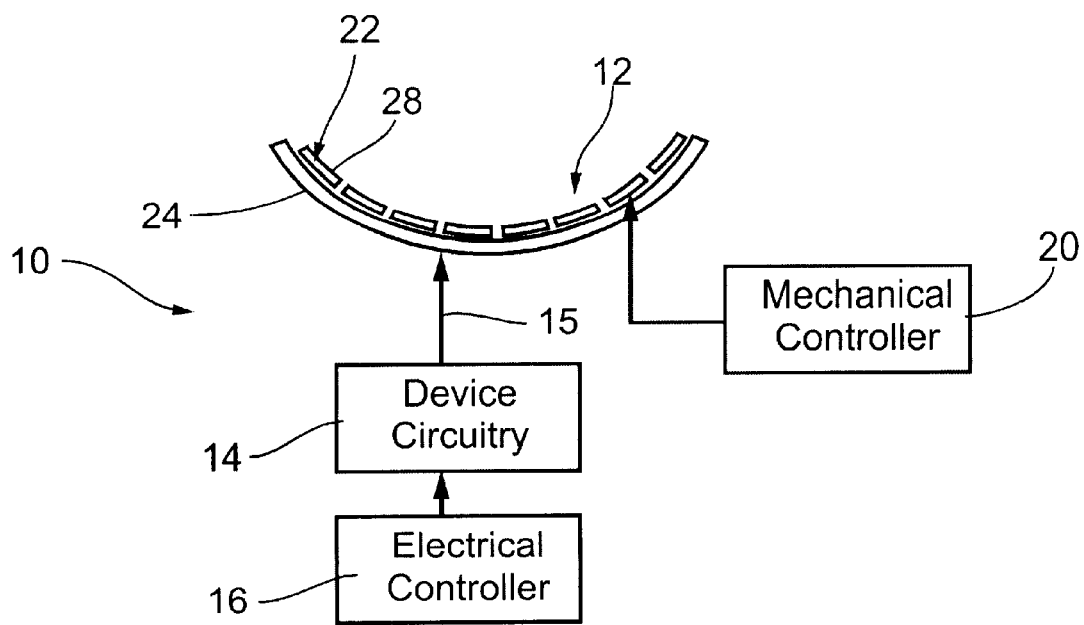
FIG. 2 is a schematic diagram of a control system for a focused ultrasound transducer array, such as the transducer array shown in FIG. 1.

Turning now to the drawings, FIGS. 1 and 2 show a preferred embodiment of a system 10 for performing a therapeutic procedure using focused ultrasound, in accordance with the present invention. The system 10 generally includes a transducer array 12, drive circuitry 14 for providing electrical drive signals 15 to the transducer array 12, and an electrical controller 16 for controlling the drive signals 15 provided by the drive circuitry 14. In addition, the system 10 includes a plurality of actuators 18 coupled to the transducer array 12 for moving, steering, or otherwise adjusting the orientation of transducer elements on the transducer array 12, and a mechanical controller 20 for controlling the actuators 18. Alternatively, a single controller (not shown) may be provided that may control both the drive circuitry and the actuators.

The transducer array 12 preferably includes a plurality of sub-arrays 22 that are movably attached to a support structure 24. Each sub-array 22 includes an acoustic emission surface 28 that may be divided into a plurality of transducer elements 29. Each sub-array 22 may be movable with respect to one another and the support structure 24 to allow adjustment of the orientation of the acoustic emission surface 28. For example, each sub-array 22 may be pivotably fixed to the support structure 24 by a two-dimensional gimbal apparatus 26, such as that shown in FIG. 1C. Thus, each sub-array 22 may be movable in one or two substantially orthogonal angular directions with respect to a central axis 30 or tangent line that is substantially normal to the support structure 24.

The transducer elements 29 are generally formed from piezoelectric material, constructed as known in the art, such that they emit acoustic energy from the acoustic emission surface 28 when excited by electrical signals from the drive circuitry 14. In a preferred embodiment, the transducer elements 29 and/or the acoustic emission surface 28 are substantially planar, although they may also be provided in a concave shape, or any other shape to provide a desired emission pattern.

In one preferred embodiment, the transducer array 12 may have an overall concave or bowl shape, and preferably a substantially hemispherical shape, such that the transducer array 12 generally defines a portion of a sphere. Such a configuration may be particularly useful for treating regions within a patient's skull. Alternatively, for treating other regions of a patient's anatomy, the transducer array 12 may define a portion of a cylinder or may have a substantially flat configuration (not shown), and/or may include an outer perimeter that is generally, but not necessarily truly, circular (not shown). Thus, the transducer array may be configured to conform generally to an outer surface of a desired anatomical structure of a patient.

Preferably, the transducer array 12 has a diameter between about ten and thirty centimeters (10–30 cm), more preferably between about twenty three and thirty centimeters (23–30 cm), and a radius of curvature between about ten and thirty centimeters (10–30 cm), for example, to allow the transducer array 12 to substantially surround a desired body structure, such as a human skull, as is described further below. The transducer array 12 may be divided into between about ten and thirty (10–30) sub-arrays, with each sub-array including between about one and five (1–5) transducer elements. Each sub-array preferably, but not necessarily, includes the same number of transducer elements. An exemplary embodiment of a transducer array in accordance with the present invention may include sixteen three-element sub-arrays having an overall diameter of about ten centimeters (10 cm) and a radius of curvature of about ten centimeters (10 cm).

As best seen in FIG. 1B, each sub-array 22 is generally divided into a plurality of transducer elements 29 that may be disposed about a central axis 30. Thus, each sub-array 22 may define an "aperture" based upon the diameter (or other cross-sectional dimension) of the sub-array 22 and its focal length, as is known in the art. Because the aperture of each sub-array 22 is relatively small, each sub-array 22 may be effectively focused or steered, even if the individual transducer elements 29 are relatively large in size, e.g., between about eight and fifteen millimeters (8–15 mm).

The transducer elements 29 may have a variety of geometric shapes, such as circles, as shown, or alternatively, hexagons, triangles, squares, and the like, and may be disposed about the central axis 30, preferably, but not necessarily, in a substantially uniform or symmetrical configuration. Alternatively, each sub-array 22 may be divided into annular and/or pie-shaped transducer elements, as is known in the art.

Each of the transducer elements 29 is individually coupled to the drive circuitry 14 in a conventional manner. The drive circuitry 14 is configured to provide electrical drive signals 15 to the transducer elements 29 at one or more frequencies, preferably at radio frequencies (RF), for example, between about 0.2–10 MHz, and more preferably between about 0.5 and 2.0 MHz. When electrical drive signals 15 are provided to the transducer elements 29, the transducer elements 29 of each sub-array 22 emit acoustic, preferably ultrasonic, energy from their acoustic emission surfaces 28, as will be appreciated by those skilled in the art.

The electrical controller 16 is coupled to the drive circuitry 14 for controlling several aspects of the drive signals 15 generated by the drive circuitry 14, such as their amplitude, frequency, and/or phase. For example, the controller 16 may control the amplitude of the drive signals 15 to control the intensity of acoustic energy delivered by the transducer array 12 in a substantially conventional manner.

In addition, the controller 16 may control a phase component of the respective drive signals 15 to each respective sub-array 22 to allow electronic adjustment of a focal distance of the acoustic energy, i.e., the distance from the acoustic emission surface 28 to the center of the focal zone of the acoustic energy, as is known in the art. Additional information on controlling the phase shift of drive signals to transducer elements of a transducer array may be found in co-pending patent applications Serial Nos. 09/556,095, filed Apr. 21, 2000, 09/557,078, filed Apr. 21, 2000, and 09/626,176, filed Jul. 27, 2000, the disclosures of which are expressly incorporated herein by reference.

With particular reference to FIG. 1C, the sub-arrays 22 are also mechanically controlled to steer the acoustic energy emitted by the transducer elements 29. Generally, the actuators 18 may adjust the overall orientation of the respective sub-arrays, preferably in one or more substantially orthogonal directions. For example, with respect to a sub-array 22 pivotably fixed by a gimbal apparatus 26, a mechanical actuator 18 may be coupled to an outer edge of the sub-array 22 that may be directed substantially parallel to the central axis 30, thereby pivoting the sub-array 22 about an axis substantially perpendicular to the central axis 30. If additional degrees of freedom are desired, as is preferred, a second mechanical actuator (not shown) may be coupled to the sub-array at a point approximately ninety degrees about the central axis 30, thereby allowing pivoting of the sub-array 22 about the central axis 30, such that the axes of rotation controlled by each of the mechanical actuators are substantially perpendicular to one another and to the central axis 30.

In a preferred embodiment, the actuators 18 are piezoelectric actuators, similar to those used in active optic devices. Additional information regarding piezoelectric actuators that may be appropriate for use with the present invention are disclosed in U.S. Pat. Nos. 4,647,808, and 5,266,863, the disclosures of which are expressly incorporated herein by reference. Alternatively, other actuators may be used that provide a desired precision of movement and response time.

A mechanical controller 20 is coupled to each of the actuators 18, thereby providing rapid and precise control of the actuators 18. The mechanical controller 20 may be a separate component than the electrical controller 16, or alternatively, both aspects of controlling the transducer array 12 may be controlled by a single controller, such as a microprocessor or other computer system.

Figure 3:
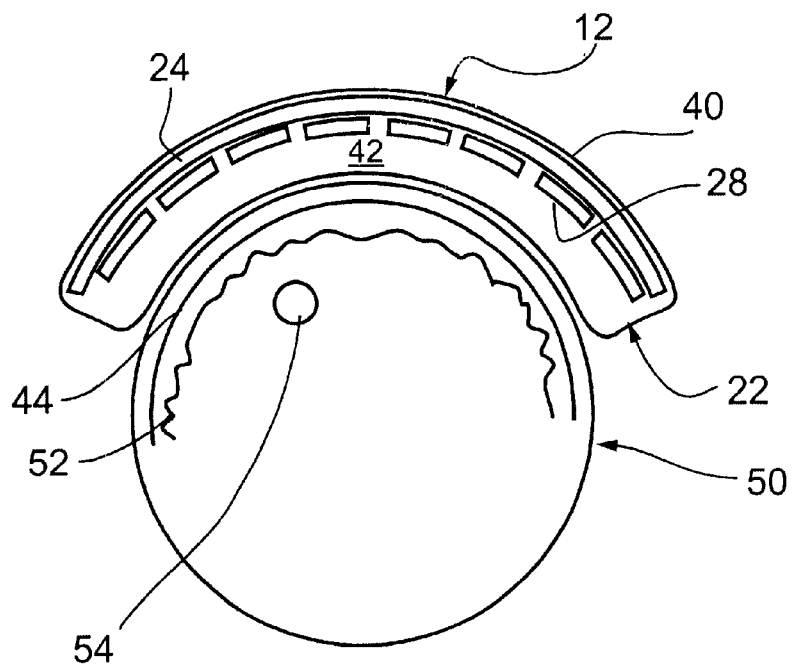
FIG. 3 is a schematic side view of a patient's head having an ultrasound transducer array disposed around the head for treating a tumor therein.

Turning to FIG. 3, the transducer array 12 is generally mounted within a fluid-filled casing 40. The casing 40 includes a chamber 42 filled with degassed water or similar acoustically transmitting fluid or gel. The support structure 24 may be secured to an outer surface of the casing 40 to substantially fix the sub-arrays 22 and transducer elements with respect to the casing, although alternatively, the actuators and/or gimbal apparatus (not shown in FIG. 3) may be secured directly to the casing 40. In addition, the actuators may be sealed or otherwise isolated from the fluid within the casing 40 in a conventional manner, as will be appreciated by those skilled in the art.

The casing 40 may include a flexible membrane 44 along its inside surface that is substantially transparent to ultrasound, such as a mylar plastic or polyvinyl chloride (PVC) sheet, or a fluid-filled bag (not shown) of such material may be provided along the inside surface. The flexible membrane 44 may conform easily to the contours of a patient 50, thereby facilitating acoustically coupling the transducer array 12 to the patient 50. Thus, the acoustic emission surfaces 28 of the sub-arrays 22 may be generally oriented towards the flexible membrane 44, for directing acoustic energy therethrough into a patient.

In addition, the system 10 may include an imaging device (not shown) for monitoring the use of the system 10 during treatment of a patient. For example, the system 10 and patient 50 may be placed within a magnetic resonance imaging (MRI) device, such as that disclosed in U.S. Pat. Nos. 5,247,935, 5,291,890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference.

During use, the casing 40 may be placed in contact with the patient 50, for example, secured or otherwise disposed around the patient's head 52, as shown in FIG. 3. Water, acoustic conducting gel, and the like (not shown) may be applied between the patient's skin and the membrane 44, thereby further enhancing acoustically coupling the patient 50 to the transducer array 12. The transducer array 12 may then be focused towards a target tissue region 54 within the patient's skull 52, such as a cancerous or benign tumor.

As an initial matter, the transducer array 12 may be calibrated, e.g., to its geometric focus, for example, to compensate for aberrations in the tissue between the transducer and the target tissue region 54. For example, a first approximation of the necessary phase corrections may be produced in an open loop fashion, e.g., from a CT scan image of the skull, taught in U.S. Provisional Patent Application Ser. No. 60/253,955, entitled "Open Loop Focussing For Ultrasound Therapy", filed on this same date, which is fully incorporated by reference. Fine tuning of the necessary phase and amplitude corrections may then be performed in a closed loop fashion, e.g., as taught in U.S. Patent Application Ser. No. 09/724,817, entitled "Systems and Methods for Focusing an Acoustic Energy Beam Transmitted Through a Non-Uniform Tissue Medium", filed on this same date, which is fully incorporated by reference.

During treatment (or even during calibration), the mechanical controller 20 generally controls the actuators 18 to mechanically steer or focus each of the sub-arrays 22 towards the target tissue region 54. In addition, the drive signals to the transducer elements may be electronically controlled to further focus the acoustic energy towards the target tissue region 54.

The transducer array 12 may be activated for sufficient time to substantially necrose the target tissue region 54, e.g., between about one and twenty (1–20) seconds, and more preferably between about three and fifteen (3–15) seconds. The transducer array 12 may then be deactivated, for example, for sufficient time to allow heat absorbed by the patient's tissue to dissipate, e.g., between about forty five and ninety (45–90) seconds, and more preferably about sixty (60) seconds or more. The transducer array 12 may then be focused on another target tissue region (not shown), for example, adjacent to the target tissue region 54, and the process repeated until an entire target tissue structure, such as a cancerous or benign tumor, is ablated.

The size and configuration of a transducer array in accordance with the present invention may be defined as required by the particular treatment. For example, each sub-array may be defined in terms of the size of each individual transducer element, the number of transducer elements per sub-array, and the degree of freedom of movement of the sub-arrays (e.g., maximum steering or pivoting angle in each direction of movement).

These values may be selected based upon the wavelength of the acoustic energy emitted by the transducer array (e.g., to keep the size of each transducer element on the order of or larger than the wavelength), a desired focal distance to reach a particular internal tissue structure), and/or the size of the tissue region to be treated. Thus, transducer elements on the order of ten millimeters (10 mm) or more may be provided to reduce the total number of transducer elements required even though acoustic energy having wavelengths of two millimeters (2 mm) or less may be used. The larger transducer element size may simplify manufacturing and/or operation of the transducer array, yet provide effective steering of the acoustic energy emitted by the transducer array.

Another parameter that may be selected based upon a particular clinical application is the maximum angle of pivoting of the sub-arrays. The maximum pivot angle, however, may be limited by physical constraints, such as the size of the sub-arrays, the distance between the sub-arrays and the support structure, the size of the casing within which the transducer array is disposed, and the like, as will be appreciated by those skilled in the art. For example, maximum pivot angles of between about thirty and ninety (30–90) degrees may be selected based upon the particular geometry of the array, e.g., to minimize the risk of the acoustic energy beam emitted from one sub-array being at least partially obstructed by an adjacent sub-array.

A transducer in accordance with the present invention may be used to treat internal tissue regions within a variety of anatomical structures. For example, the transducer may be provided in a generally hemispherical or other configuration that may substantially conform to an exterior surface of a patient. Mechanical steering of individual sub-arrays may substantially eliminate all or a portion of a mechanical positioning system, such as those used for moving conventional spherical cap transducers. For treating some body regions, such as the pelvic region, this may facilitate use of larger transducer elements, e.g., on the order of one centimeter or larger, that may be provided individually on steerable sub-arrays. Each individual transducer element may thus be steered towards a target tissue region, thereby substantially simplifying the number of transducer elements needed, depending upon the desired quality of the focal zone. For example, a transducer array, having a cross-section or diameter of about ten centimeters (10 cm) or more, may include as few as fifteen (15) transducer elements, that may be driven at a frequency of about 1.5 MHz, yet may be capable of effectively focusing acoustic energy at a desired size target tissue region.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for performing a therapeutic procedure in a target region of a patient using focused ultrasound, comprising:

a transducer array comprising a plurality of sub-arrays, each sub-array defining an acoustic emission surface and including one or more transducer elements configured for emitting acoustic energy from the acoustic emission surface, each sub-array being independently movable with respect to one another about at least two respective axes of rotation;

drive circuitry coupled to the transducer elements, the drive circuitry configured for providing respective drive signals to the transducer elements, whereby the transducer elements may emit acoustic energy from their respective acoustic emission surfaces; and a mechanical controller coupled to the sub-arrays and configured for moving the sub-arrays about the at least two respective axes of rotation to adjust an orientation of the acoustic emission surfaces of respective sub-arrays to facilitate focusing of the acoustic energy emitted by the transducer elements towards the target region.

2. The system of claim 1, wherein the transducer array comprises a support structure, the sub-arrays being attached to the support structure.

3. The system of claim 2, wherein the support structure has a generally concave shape.

4. The system of claim 2, wherein the sub-arrays are pivotably fixed to the support structure.

5. The system of claim 4, wherein the mechanical controller comprises an actuator coupled to each of the sub-arrays for mechanically pivoting the respective sub-array to adjust its orientation.

6. The system of claim 5, wherein the mechanical controller comprises a pair of actuators coupled to each sub-array, the pair of actuators configured for pivoting the respective sub-array in substantially orthogonal directions.

7. The system of claim 5, wherein the actuator comprises a piezoelectric actuator.

8. The system of claim 1, wherein each sub-array includes a gimbal apparatus pivotably fixing the sub-arrays with respect to one another.

9. The system of claim 1, further comprising an electrical controller coupled to the drive circuitry, the electrical controller configured for controlling phase shift values of the respective drive signals to further focus the acoustic energy emitted by the transducer elements towards the target region.

10. A system for performing a therapeutic procedure in a target region of a patient using focused ultrasound, comprising:
    a transducer array comprising a plurality of sub-arrays, each sub-array defining an acoustic emission surface and including one or more transducer elements configured for emitting acoustic energy from the acoustic emission surface, each sub-array being independently movable with respect to one another;
    drive circuitry coupled to the transducer elements, the drive circuitry configured for providing respective drive signals to the transducer elements, whereby the transducer elements may emit acoustic energy from their respective acoustic emission surfaces;
    a mechanical controller coupled to the sub-arrays and configured for moving the sub-arrays to adjust an orientation of the acoustic emission surfaces of respective sub-arrays to facilitate focusing of the acoustic energy emitted by the transducer elements towards the target region; and
    an electrical controller coupled to the drive circuitry, the electrical controller configured for controlling phase shift values of the respective drive signals to further focus the acoustic energy emitted by the transducer elements towards the target region, wherein the electrical controller is configured for controlling the phase shift values of the drive signals to the transducer elements of a respective sub-array for compensating for aberrations in intervening tissue between the transducer and the target tissue.

11. The system of claim 1, wherein the transducer array is mounted within a fluid-filled casing.

12. The system of claim 11, wherein the casing has a substantially concave inner contact surface configured for substantially engaging a head of a patient.

13. The system of claim 12, wherein the sub-arrays are arranged within the casing such that the acoustic emission surfaces of the sub-arrays are generally oriented towards the inner contact surface.

14. A method for performing a therapeutic procedure in a target tissue region of a patient using focused ultrasound, the method comprising:
    providing a transducer array comprising a plurality of sub-arrays, each sub-array including one or more transducer elements, each sub-array being independently movable relative to one another about two respective axes of rotation for adjusting an orientation of the sub-arrays with respect to one another;
    driving the transducer elements with respective drive signals such that the transducer elements emit acoustic energy towards a target region; and moving the sub-arrays with respect to one another about the two respective axes of rotation to focus the acoustic energy generated by the transducer elements towards the target region.

15. The method of claim 14, wherein the sub-arrays comprise an acoustic emission surface from which the transducer elements emit the acoustic energy, and wherein the step of moving the sub-arrays comprises pivoting the sub-arrays about a fixed point to adjust an angular orientation of their respective acoustic emission surfaces.

16. The method of claim 15, wherein the step of pivoting the sub-arrays comprises pivoting the sub-arrays about two respective axes of rotation that are substantially perpendicular to one another.

17. The method of claim 14, wherein the transducer array is acoustically coupled to a skull such that the target region is a tissue structure within the skull.

18. A method for performing a therapeutic procedure in a target tissue region of a patient using focused ultrasound, the method comprising:
    providing a transducer array comprising a plurality of sub-arrays, each sub-array including one or more transducer elements, each sub-array being movable relative to one another for adjusting an orientation of the sub-arrays with respect to one another, the transducer array being acoustically coupled to a skull such that the target region is a tissue structure within the skull;
    driving the transducer elements with respective drive signals such that the transducer elements emit acoustic energy towards a target region; and
    moving the sub-arrays with respect to one another to focus the acoustic energy generated by the transducer elements towards the target region;
    wherein the step of driving the transducer elements comprises controlling relative phase shift values of the respective drive signals to compensate for skull phase aberrations.

19. The method of claim 14, wherein the transducer elements are driven with respective drive signals such that the acoustic energy emitted by the transducer element substantially ablates the tissue structure.

20. The method of claim 14, wherein the transducer elements are driven with respective drive signals, and wherein phase shift values of drive signals driving the transducer elements of each sub-array is controlled such that the acoustic energy emitted by the respective sub-array is focused at a predetermined focal distance or is focused at a focal zone having a predetermined shape.

21. A system for performing a therapeutic procedure in a target region of a patient using focused ultrasound, comprising:

a transducer array comprising a plurality of sub-arrays, each sub-array defining an acoustic emission surface and including a plurality of transducer elements configured for emitting acoustic energy from the acoustic emission surface, each sub-array being independently movable with respect to one another;

drive circuitry coupled to the transducer elements, the drive circuitry configured for providing respective drive signals to the transducer elements, whereby the transducer elements may emit acoustic energy from their respective acoustic emission surfaces; and a mechanical controller coupled to the sub-arrays and configured for moving the sub-arrays to adjust an orientation of the acoustic emission surfaces of respective sub-arrays to facilitate focusing of the acoustic energy emitted by the transducer elements towards the target region.

22. The system of claim 21, wherein each sub-array is pivotable about two respective axes of rotation.

23. The system of claim 22, wherein the two respective axes of rotation that are substantially perpendicular to one another.

* * * * *